United States Patent [19]

Gill et al.

[11] Patent Number: 4,469,888
[45] Date of Patent: Sep. 4, 1984

[54] PROCESS FOR THE PREPARATION OF 2,4-DINITRO-2,4-DIAZAPENTANE

[75] Inventors: Robert C. Gill, White Plains; George W. Nauflett, Fort Washington, both of Md.

[73] Assignee: The United States of America as represented by the Secretary of the Navy, Washington, D.C.

[21] Appl. No.: 391,902

[22] Filed: Jun. 25, 1982

[51] Int. Cl.$^3$ .......................................... C07C 111/00
[52] U.S. Cl. .................................... 564/109; 564/107
[58] Field of Search ............................... 564/107, 109

[56] References Cited

U.S. PATENT DOCUMENTS 2,856,429 10/1958 Sauer ................................ 564/109

Primary Examiner—Robert V. Hines
Attorney, Agent, or Firm—Robert F. Beers; Kenneth E. Walden; John C. LaPrade

[57] ABSTRACT

The invention is a process for reacting methylnitramine with formaldehyde in a halogenated solvent and reacting the methylnitramine with formaldehyde in the presence of a strong sulfuric acid catalyst at certain specific temperatures to yield a final product having a yield rate of 70% or greater dimethylmethylenedinitraamine.

5 Claims, No Drawings

PROCESS FOR THE PREPARATION OF 2,4-DINITRO-2,4-DIAZAPENTANE

BACKGROUND OF THE INVENTION

In the prior art there are at least three known methods for the preparation of 2,4-dinitro-2,4-diazopentane or dimethylmethylenedinitramine hereinafter known as DMMD.

In the first of these methods two moles of methylnitramine are reacted with formaldehyde in the presence of a 90% sulfuric acid catalyst. This method according to Goodman, disclosed in the Journal American Chemical Society Vol. 75, page 3019 (1953) yields 39% DMMD. Goodman obtained the same yields when 82 and 90% sulfuric acid was used. The yield dropped to 13% when 74% sulfuric acid was used.

In a second known method one mole of 2-nitro-2-aza-1-propanol, hereinafter known as NAP, is reacted with one mole of methylnitramine using toluene as an azeotrope to remove water. In this reaction DMMD is recovered in a yield of 43%.

In the third known reaction well known in the prior art the ammonium salt of methylnitramine is reacted with chlorodimethylamine nitrate using dimethylformamide as a solvent and catalytic agent to yield DMMD and ammonium chloride. The yield of DMMD in this reaction is limited to 27% and is disclosed in Chemical Abstracts Vol. 65, entries 10483d and 10484c.

In short the low yields known in the prior art have prevented this DMMD from becoming a commercial explosive or energetic compound because of great cost associated with low yield.

SUMMARY OF THE INVENTION

The inventors in this case have invented a process for reacting two moles of methylnitramline with formaldehyde or equivalent substance in a suitable halogenated solvent wherein the solvent works in the presence of sulfuric acid to prevent the further decomposition the DMMD. The use of the particular halogenated organic solvents according to the processes of this invention also prevents the further decomposition of the starting material methylnitramine and the intermediate NAP. Accordingly, it is one object of this invention to provide a novel method of reacting methylnitramine with NAP under such reaction conditions including halogenated solvents that will result in a much higher yield of the end product DMMD and protect the DMMD from the catalytic action of sulfuric acid or any other of the reactants or catalyst present.

It is one further object of the invention to utilize certain specified particular solvents to prevent sulfuric acid from decomposing methylnitramine.

It is another object of the invention to increase the yield of DMMD by the utilization of certain specific solvents in a reaction.

DESCRIPTION OF THE PREFERRED EMBODIMENT

1. DMMD Preparations

A. Standard Preparation—Nearly all the 100 g of DMMD produced thus far has been made by reacting methylnitramine with paraformaldehyde in sulfuric acid. Modifications to the procedure given in the literature have resulted in an increase in the yield from 40% to 70% with improved purity of the product as evidenced by an increase in melting point from 48°-50° to 54°-55° C. Details of these modification in the synthesis of DMMD are shown in Table I. The general procedures are given below.

General Procedure—To a solution of 2.5 g of paraformaldehyde in 160 ml of sulfuric acid, cooled to −6° C., is added with vigorous stirring 9.0 g of methylnitramine. A small amount of methylene chloride is either added to the acid layer or used to dissolve the methylnitramine. After the mixture is stirred for a specified time, it is poured onto a large quanity of ice. Additional methylene chloride is then added and the two layers separated. The acid layer is extracted two times with 50 ml portions of methylene chloride. Then the combined extracts are washed twice with 50 ml portions of water. Removal of the solvent in a rotating evaporator leaves DMMD.

2. Preparation of 2-nitro-2-aza-1-propanol was accomplished according to the procedure set forth by Ganeev, et al. in Zhurnal Org. Klim, Vol. 7, p. 623–624 (1971) (English translation).

Equal molecular quantities of NAP and methylnitramine are used in procedure 2 and all the other conditions are the same as procedure 1.

TABLE I

Preparation of Dimethylmethylenedinitramine (DMMD)

| 9.00 g of Methylnitramine ($CH_3NHNO_2$) | Paraformaldehyde (g) | $H_2SO_2$ Volume (ml) | $H_3SO_4$ Acid Strength | Method of Addition | Reaction Period (min.) | Yield (%) | Yield (grams) | Melting Point (°C.) |
|---|---|---|---|---|---|---|---|---|
| Crystals (no solvent) | 2.5 | 160 | 90% | $CH_3NHNO_2$ crystals to acid/$CH_2Cl_2$ solution | 10 | 62.5*<br>55.4 | 6.07*<br>5.38 | 48.0–51.0*<br>53.5–55.2 |
| Crystals (no solvent) | 2.5 | 160 | 90% | $CH_3NHNO_2$ crystals to acid/$CH_2Cl_2$ solution | 20 | 66.2<br>— | 6.43<br>— | 54.3–55.2<br>55.0–55.3** |
| Crystals (no solvent) | 2.5 | 160 | 90% | $CH_3NHNO_2$ crystals to acid/$CH_2Cl_2$ solution | 30 | 65.2 | 6.33 | 47.0–49.0 |
| Dissolved in 20 ml of $CH_2Cl_2$ | 2.5 | 160 | 90% | $CH_3NHNO_2/CH_2CL_2$ mixture to acid solution | 20 | 62.3 | 6.05 | 48.2–50.5 |
| Dissolved in 10 ml of $CH_2Cl_2$ | 2.5 | 160 | 90% | $CH_3NHNO_2/CH_2Cl_2$ mixture to acid solution | 20 | 69.7 | 6.77 | 54.2–54.8 |
| Dissolved in 10 ml of $CH_2Cl_2$ | 2.5 | 160 | 95–98% (concentrated) | $CH_3NHNO_2/CH_2Cl_2$ mixture to acid solution | 20 | 63.1*<br>56.5 | 6.13*<br>5.49 | 51.5–52.3*<br>54.8–55.5 |

*No water wash
**Recrystallized from $CH_2Cl_2$/Hexane

Preparation of Dimethylmethylene Dinitramine (DMMD)

The class of solvents that are preferred in the preferred embodiment of this invention are the halogenated solvents such as methylene chloride, chloroform, ethylene chloride. Other well known aromatic solvents such as toluene and xylene are not as preferred as halogenated but will operate to perform the basic function of the solvent to some appreciable degree.

In the secondary aspect of the invention 2-nitro 2-aza1-propanol is used as a starting material or in the alternative may be formed in the situ by adding two mole of methylnitramine to one mole of 37% formaldehyde.

In the basic reaction formaldehyde is reacted with methylnitramine in the presence of sulfuric acid and a halogenated solvent. This reaction in the preferred embodiment is conducted in the temperature range of −20° up to but not above 0° in order to obtain a high yield usually 70% or greater.

In the alternative process disclosed, half of the methylnitramine is reacted with an equi-molar amount of formaldehyde to form NAP which is reacted with the remaining methylnitramine and sulfuric acid in the presence of a halogenated or aromatic solvent.

Again in order to obtain the best yield and the best results the reaction is best conducted at a temperature from about −20° up to 0°.

In the secondary reaction methylnitramine reacts with formaldehyde to produce 2-nitro-2-aza-1-propanol. This reaction serves to protect the end product DMMD as well as methylnitramine from the adverse reaction or conditions caused by sulfuric acid catalyst. Since only one half of the methylnitramine is present when nitroazapropanol is used it is naturally and mandatorially protected from the adverse reaction of sulfuric acid. In addition there is less decomposition because less methylnitramine is in such case exposed to the sulfuric acid.

It has been surpisingly found that time is an important factor in that the basic reaction of methylnitramine (which is in the preferred embodiment dissolved in a liquid halogenated solvent) must be exposed to the solvent and sulfuric acid for a period of at least 20 minutes in order to obtain a high yield. The preferred time of reaction will vary between 20 and 40 minutes yielding a product of DMMD usually in such reaction conditions of 70% or more.

What is claimed is:

1. The improved method for the production of dimethylmethylenedinitramine comprising the steps of dissolving methylnitramine in a suitable halogenated organic solvent selected from the group consisting of methylene chloride, chloroform and ethylene chloride and reacting the dimethylmethylenedinitramine with formaldehyde in the presence of a strong sulfuric acid catalyst for a period of at least 20 minutes at a temperature ranging from 0° C. to −20° C., to yield a final product having a yield rate of 70% or greater dimethylmethylenedinitramine.

2. The method of claim 1 wherein the methylnitramine is dissolved in a halogenated organic solvent prior to the reaction with paraformaldehyde.

3. The method of claim 1 wherein the sulfuric acid is mixed with a halogenated organic solvent prior to its introduction to reaction chamber.

4. The method of claim 1 wherein the reaction period varies between 20 and 40 minutes and the yield of DMMD is equal to or in excess of 70%.

5. The method of claim 1 wherein methyl nitramine is reacted with formaldehyde to yield 2-nitro--2-aza-1-propanol which is subsequently reacted with methylnitramine in a halogenated organic solvent in the presence of concentrated sulfuric acid.

* * * * *